United States Patent [19]

Coffen

[11] 4,026,901

[45] May 31, 1977

[54] CONVERSION OF 4-LOWER ALKYLOXAZOLE-5-CARBOXAMIDE TO 4-LOWER ALKYL-5-CYANOOXAZOLES

[75] Inventor: David Llewellyn Coffen, Glen Ridge, N.J.

[73] Assignee: Hoffmann-La Roche Inc., Nutley, N.J.

[22] Filed: Apr. 30, 1975

[21] Appl. No.: 573,226

[52] U.S. Cl. .................. 260/307 R; 260/465 B
[51] Int. Cl.² .................................. C07D 263/34
[58] Field of Search ............... 260/307 R, 465 B

[56] References Cited

UNITED STATES PATENTS

| | | | |
|---|---|---|---|
| 2,054,088 | 9/1936 | Linstead et al. | 260/99.30 |
| 3,222,374 | 12/1965 | Chase | 260/307 |

OTHER PUBLICATIONS

Brown et al., "Quantitative Chemistry" 1964, pp. 473–475.

Primary Examiner—Donald G. Daus
Assistant Examiner—David E. Wheeler
Attorney, Agent, or Firm—Samuel L. Welt; Bernard S. Leon; Richard A. Gaither

[57] ABSTRACT

A process is disclosed whereby 4-lower alkyl-5-cyanooxazoles, are obtained by vapor phase catalytic dehydration of 4-lower alkyloxazole-5-carboxamides.

9 Claims, No Drawings

CONVERSION OF 4-LOWER ALKYLOXAZOLE-5-CARBOXAMIDE TO 4-LOWER ALKYL-5-CYANOOXAZOLES

BACKGROUND OF THE INVENTION

Pyridoxine (vitamin $B_6$) is a well known vitamin normally used as an adjunct in prophylaxis and treatment of multiple vitamin B complex deficiencies. It is also used in dermatoses, neuromuscular and neurological diseases.

An important synthetic procedure for pyridoxine involves the use of 4-methyl-5-cyanooxazole as a key intermediate. A typical synthetic procedure is that of Kimel et al., disclosed in U.S. Pat. No. 3,250,778, wherein 4-methyl-5-cyanooxazole is condensed with a 4,7-dihydro-1,3-dioxepin followed by acid hydrolysis of the resultant product to form pyridoxine. However, there is a continuing search to find more efficient and economical methods of producing the 4-methyl-5-cyanooxazole intermediate. Prior methods of preparing this intermediate have involved either heating 4-methyloxazole-5-carboxamides with phosphorous pentoxide or utilizing conventional amide dehydrating agents, such as phosphorous oxyhalides, to form the corresponding nitriles. These procedures were fraught with disadvantages such as charring, poor yields, equipment corrosion and unwanted by-products. One solution to the above problems is disclosed in a patent to Chase, U.S. Pat. No. 3,222,374, wherein the 4-lower alkyl-5-carboxamide is reacted with phosphorus pentoxide in the presence of a solvent such as quinoline. The following reaction scheme is illustrative of the preparation of 4-lower alkyl-5-cyanooxazole employing the Chase improvement:

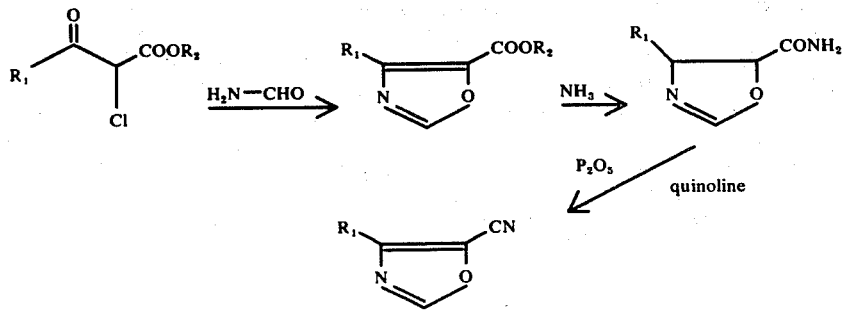

wherein $R_1$ and $R_2$ are lower alkyl.

A disadvantage of the above procedure is that the conversion of the amide group to a nitrile is very expensive, thus resulting in a loss of economy and efficiency. An additional disadvantage is that disposal of spent $P_2O_5$ and quinoline pose a serious pollution problem.

The instant invention provides to the art a method for the preparation of 4-lower alkyl-5-cyanooxazoles which is efficient, economical and free of the disadvantages of the procedures known heretofore.

SUMMARY OF THE INVENTION

In accordance with the instant invention, it has been found that a compound having the formula:

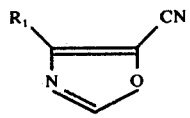

wherein $R_1$ is as defined above; may be prepared by subjecting a compound of the formula:

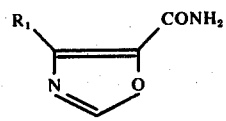

to catalytic dehydration. This dehydration is accomplished by introducing compound I, in the vapor phase, into a fixed-bed catalytic reactor such as a packed column. Compound I may also be introduced to the fixed-bed catalytic reactor by employing other standard techniques, e.g., introducing compound I in the liquid phase under pressure. A preferred procedure is to introduce compound I in the vapor phase. The column temperature ranges from about 200°-600° C., preferably 350° C. to 450° C., and is packed with a material that catalyzes the dehydration. Yields of nitrile up to about 90% are achieved by the novel process disclosed herein.

DETAILED DESCRIPTION OF THE INVENTION

As used throughout the specification, the term "lower alkyl" is intended to connote a straight or branched chain hydrocarbon group containing 1 to 6 carbon atoms such as methyl, ethyl, isopropyl, butyl and the like.

As used herein, the term "amide" refers to 4-lower alkyloxazole-5-carboxamide. The term "nitrile" as used herein, connotes a 4-lower alkyl-5-cyanooxazole.

A compound of formula I is converted to a compound of formula II by first subjecting the amide to sublimation conditions. The resulting amide vapor is then passed through a heated packed column. The materials comprising the column packing, catalyze the dehydration of the amide to the nitrile. The resulting nitrile and water are collected in a suitable vessel with subsequent separation and purification of the nitrile.

The catalytic column packing material usable in the instant invention may be selected from molecular sieve 5A, silica, $P_2O_5$ supported on silica, $P_2O_5$ supported on charcoal, unglazed procelain chips α-alumina pellets, $P_2O_5$ supported on α-alumina pellets, $P_2O_5$ supported on molecular sieve 5A, and $P_2O_5$ supported on porous carborundum. It has been found that a small amount of phosphorus pentoxide, comprising from about 1% to about 10% by weight of the total catalyst enhances the catalytic effect of the column packing materials when adsorbed thereon. Basic packing materials such as γ-alumina, soda-lime and calcium chloride are less suitable then materials which are acidic or neutral. The packing materials utilized herein may also have adsorbed thereon precursors of $P_2O_5$, e.g., phorphoric acid, which upon appropriate treatment of the thus adsorbed material, by means known in the art, would result in $P_2O_5$ treated catalysts mentioned hereinabove.

The columns utilized herein may be employed for successive dehydrations. The number of times a column may be reused will depend upon the packing material employed. It has been found that successive dehydrations employing the same column have resulted in constant nitrile yields of about 90%.

An attractive feature of the instant process is that it can be carried out either continuously or batchwise. The flexibility of this process is further enhanced by the reusability of the columns, thus resulting in a significant savings in time and expense.

The length and diameter of the columns employed are critical features of this invention. It is important that a column length be selected in relation to the flow rate of the amide vapor such that the contact time between the vapor and the catalyzed packing material be optimized. If the column is too short, the amide will sublime through unchanged. If the column is too long, the yield of nitrile is substantially lowered or nil. It is equally important that a column diameter be selected such that the catalyst bed is uniformly heated. Uniform heating of the column avoids the formation of thermal gradients (i.e., cool channels) within the catalyst bed. Thermal gradients within the catalyst bed will result in incomplete dehydration of the amide. Columns having a length to diameter ratio ranging from about 5 to about 65, preferably about 40, insure optimal contact between the amide vapor and the fixed bed catalytic reactor. Other parameters, such as flow rates of the amide vapor, may be readily determined in accordance with procedures known to the art.

It is important that the column temperature be maintained at from about 200° C. to about 600° C. If the column temperature is below 200° C., the amide will pass through the column unchanged. If the temperature is above 600° C., decomposition of the amide will occur, producing HCN and other volatile pyrolysis products. Standard heating means may be employed to insure proper column temperature.

The following non-limiting examples illustrate the instant invention.

EXAMPLE 1

Preparation of $P_2O_5$ Treated Column Packing Material

Silica gel doped with $P_2O_5$ was prepared by shaking 50 g. of silica gel (6-16 mesh size) with 5 g. of $P_2O_5$ powder. The mixture was thoroughly mixed by shaking in a stoppered round bottom flask. This produced a free-flowing silica gel with a "wet" appearance on the surface of the granules.

Molecular sieves 5A doped with $P_2O_5$ was prepared by rotating a flask containing 30 g. of molecular sieves and 3 g. of $P_2O_5$ overnight.

Granular charcoal (47 g.) was thoroughly mixed with $P_2O_5$ (3 g.) and the mixture sprayed with a fine mist of water. The water was subsequently removed by heating the material under vacuum at a temperature of about 300°–350° C. and 25–30 mmHg.

A mixture of 100 g. of *Chemetron T-375 α-alumina ⅛ inch. × ⅛ inch. tablets and 6 g. of $P_2O_5$ was shaken overnight to provide a $P_2O_5$ doped α-alumina catalyst.
*Available from Chemetron Corporation, Chicago, Ill.

**Girdler T-869 silica carrier (⅛ inch, extrusions) 50 g. were shaken with 3 g. of $P_2O_5$ until the $P_2O_5$ appeared to be completely absorbed.

EXAMPLE 2

This example illustrates the obtention of nitrile when dehydrating the amide in accordance with the instant invention.

The dehydrations were carried out by surrounding a reservoir flask containing the amide by a Kugelrohr oven heated to about 200° C. The reservoir flask is connected to a quartz glass column packed with one of the materials tabulated below. The column is in turn connected to a collector through which the dehydration products are conducted to a cooling flask and subsequently purified. The column pressure is reduced to 15–30 mmHg by means of a water aspirator.

Columns of differing lengths were employed. Column 1 had a packable length of 10.5 cm and an outside diameter of 2.15 cm. Column 2 had a packable length of 26 cm and an outside diameter of 3.15 cm. Column 3 had a packable length of 40 cm and an outside diameter or 1.2 cm. The following table illustrates the yields of nitrile obtained employing the process of the instant invention.

Table 1

| Weight of Amide Dehydrated | Column Packing | Column used (see Example 1) | Yield of Nitrile |
| --- | --- | --- | --- |
| 3 g. | Molecular sieves 5A | 1 | 56% |
| 10 g. | Molecular sieves 5A/$P_2O_5$ | 2 | 70.0% |
| 3 g. | "Drierite" ($CaSO_4$) | 1 | 39% |
| 3 g. | Silica gel (6-16 mesh) | 1 | 61% |
| 30 g. | Silica gel/$P_2O_5$ | 3 | 90.4% |
| 10 g. | Charcoal/$P_2O_5$ | 2 | 88.7% |
| 10 g. | $P_2O_5$ on Girdler T-869 silica carrier | 1 | 86.6% |
| 10 g. | Girdler T-869 silica carrier | 1 | 83.5% |
| 25.2 g. | Chemetron T-375 α-alumina pellets | 3 | 92.5% |
| 10 g. | Unglazed porcelain chips | 2 | 53.7% |
| 30 g. | Porous carborundum/$P_2O_5$ | 3 | 96% |

EXAMPLE 3

Purification of Nitrile

In order to obtain accurate data on yields, the crude nitrile was purified in the following way. The flask and adaptor used to collect the crude nitrile were rinsed with methylene chloride and the diluted nitrile and dried over anhydrous sodium sulfate. The drying agent was filtered off and thoroughly washed with methylene chloride. Most of the methylene chloride was distilled from the filtrate through a short Vigreaux column. Aspirator vacuum was then applied and the nitrile collected at 64° C/25 mmHg. Generally there was no appreciable pot residue. The distillation apparatus was heated with a heat gun to drive over the last drops of nitrile. The purity of the distilled product was checked by recording ir and nmr spectra and comparing them with those of a redistilled sample whose purity had been verified by glc analysis.

EXAMPLE 4

The following example illustrates the reusability of a typical column employed in the instant invention.

Following the procedure of Example 2, five 30 g. portions of amide were successively dehydrated employing a column packed with 30 g. of 10% $P_2O_5$ treated silica gel. The yields of nitrile are illustrated in Table II.

Table II

| Weight of Amide Dehydrated | Yield of Nitrile obtained |
| --- | --- |
| 30 g. | 86.3% |
| 30 g. | 90.4% |
| 30 g. | 90.4% |
| 30 g. | 91.0% |
| 30 g. | 90.0 |

It can be readily observed that about 150 gms. of amide can be dehydrated employing about 30 g. of packing material (i.e., about 5:1 ratio) with no loss of column efficiency.

I claim:

1. A process for the conversion of a compound having the formula:

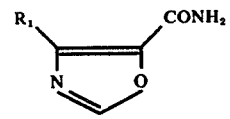

wherein $R_1$ is lower alkyl; to a compound having the formula:

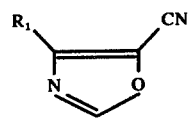

wherein $R_1$ is as defined above; by catalytic dehydration consisting essentially of introducing compound I into a column packed with a solid catalyst selected from the group consisting of molecular sieve 5A, silica, α-alumina, $P_2O_5$ supported on silica, $P_2O_5$ supported on molecular sieve 5A, $P_2O_5$ supported on α-alumina, $P_2O_5$ supported on charcoal and $P_2O_5$ supported on porous carborundum, said column having a length to diameter ratio of from about 5 to about 65 and being heated to a temperature of from 200° C. to 600° C.

2. A process according to claim 1 wherein said catalyst is silica.

3. A process according to claim 2 wherein said catalyst is $P_2O_5$ supported on silica.

4. A process according to claim 1 wherein said catalyst is $P_2O_5$ supported on charcoal.

5. A process according to claim 4 wherein said catalyst is $P_2O_5$ supported on α-alumina.

6. A process according to claim 1 wherein said catalyst is $P_2O_5$ supported on molecular sieve 5A.

7. A process according to claim 1 wherein said catalyst is $P_2O_5$ supported on porous carborundum.

8. A process according to claim 1 wherein the column temperature is from about 350° C. to about 450° C.

9. A process according to claim 1 wherein the column length to diameter ratio is about 40.

* * * * *